(12) United States Patent
Huber et al.

(10) Patent No.: US 12,257,033 B2
(45) Date of Patent: Mar. 25, 2025

(54) SYSTEM, COMPUTER SYSTEM AND COMPUTER PROGRAM FOR DETERMINING A CARDIOVASCULAR PARAMETER

(71) Applicant: Pulsion Medical Systems SE, Feldkirchen (DE)

(72) Inventors: Wolfgang Huber, Gmund (DE); Mark Konrad, Munich (DE); Sergej Kammerzell, Munich (DE)

(73) Assignee: Pulsion Medical Systems SE, Feldkirchen (DE)

( * ) Notice: Subject to any disclaimer, the term of this patent is extended or adjusted under 35 U.S.C. 154(b) by 966 days.

(21) Appl. No.: 17/287,046

(22) PCT Filed: Oct. 21, 2019

(86) PCT No.: PCT/EP2019/078571
§ 371 (c)(1),
(2) Date: Nov. 3, 2021

(87) PCT Pub. No.: WO2020/083836
PCT Pub. Date: Apr. 30, 2020

(65) Prior Publication Data
US 2022/0079453 A1 Mar. 17, 2022

(30) Foreign Application Priority Data
Oct. 22, 2018 (DE) ...................... 10 2018 008 356.0

(51) Int. Cl.
*A61B 5/0205* (2006.01)
*A61B 5/029* (2006.01)
*A61B 5/0295* (2006.01)

(52) U.S. Cl.
CPC ............ *A61B 5/0205* (2013.01); *A61B 5/029* (2013.01); *A61B 5/0295* (2013.01)

(58) Field of Classification Search
None
See application file for complete search history.

(56) References Cited

U.S. PATENT DOCUMENTS

| 5,526,817 A | 6/1996 | Pfeiffer et al. |
| 2011/0004141 A1* | 1/2011 | Zhang ..................... A61M 1/16 604/6.13 |

(Continued)

FOREIGN PATENT DOCUMENTS

DE 4214402 A1 11/1993

OTHER PUBLICATIONS

International Search Report for International Application No. PCT/EP2019/078571 mailed Jan. 13, 2020.

*Primary Examiner* — Susan S Su
*Assistant Examiner* — Katherine-Ph Minh Pham
(74) *Attorney, Agent, or Firm* — Patterson + Sheridan, LLP

(57) ABSTRACT

The system interacts with an apparatus for extracorporeal blood treatment, which is connected to the venous vascular system of a patient via an inflow line and an outflow line. Temperature influencing means for causing an initial local temperature deviation $T_1$ in the vicinity of a first point of the vascular system, as a result of which a traveling temperature change is introduced into the blood flow of the patient, a first temperature sensor for measuring the local temperature of the blood at a second point of the vascular system downstream of the first point, and a second temperature sensor for measuring the local temperature of the blood in the inflow line are provided. A computer system records the local blood temperature measured at the second point and at the inflow line, in each case as a function of time, and ascertains and evaluates a first and second thermodilution curve ($TDK_1$, $TDK_2$). A temperature deviation TEKBV, which is to be allocated to the extracorporeal blood treatment apparatus, is (Continued)

determined from the second thermodilution curve, and $T_1$ and TEKBV are correlated to one another for the purposes of determining the cardiovascular parameter.

12 Claims, 1 Drawing Sheet

(56) References Cited

U.S. PATENT DOCUMENTS

| | | | | |
|---|---|---|---|---|
| 2011/0105911 | A1* | 5/2011 | Borg | A61B 5/028 600/481 |
| 2015/0316404 | A1* | 11/2015 | Krivitski | G01F 22/02 702/19 |
| 2016/0346452 | A1* | 12/2016 | Gilbert | A61M 1/369 |

* cited by examiner

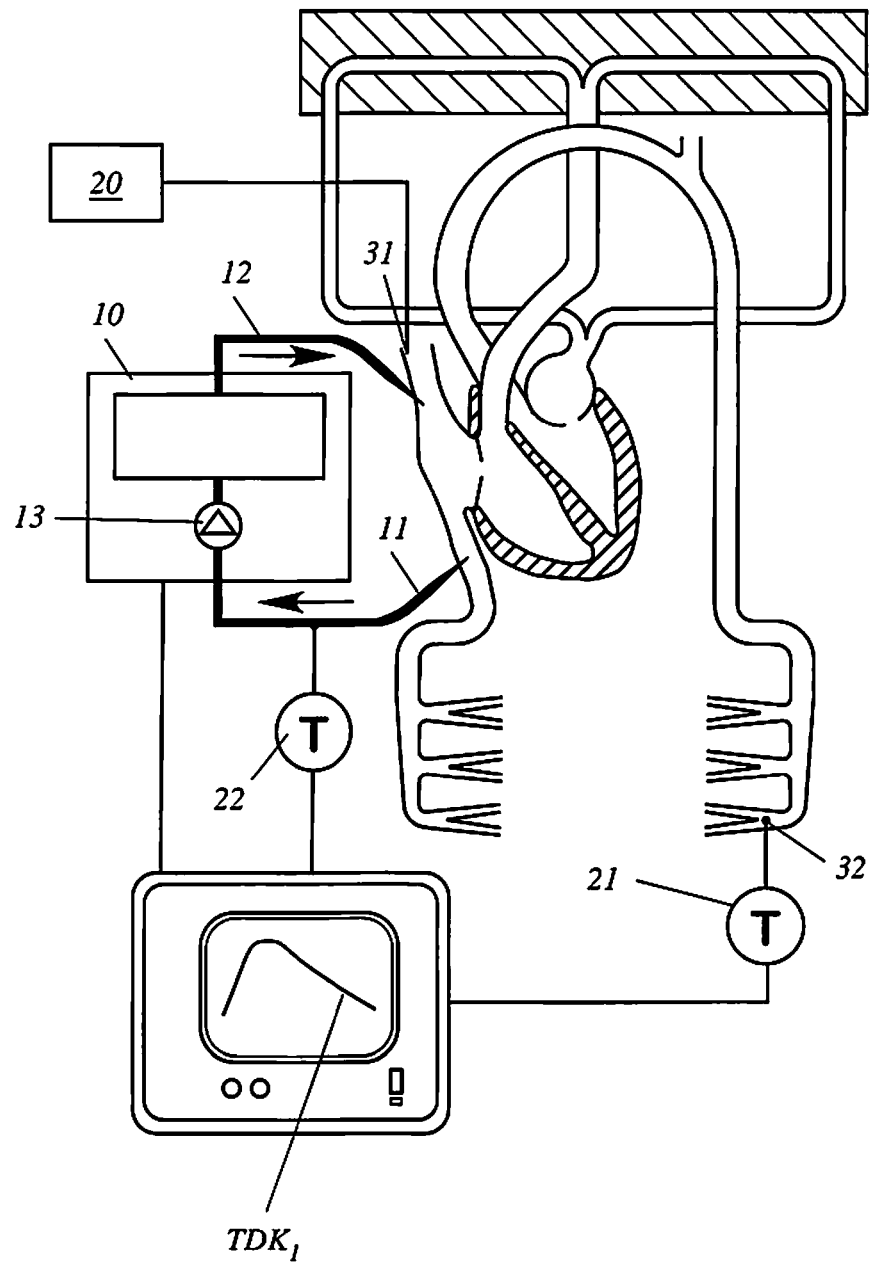

SYSTEM, COMPUTER SYSTEM AND COMPUTER PROGRAM FOR DETERMINING A CARDIOVASCULAR PARAMETER

CROSS-REFERENCE TO RELATED APPLICATIONS

This application is the United States national phase application of International Application No. PCT/EP2019/078571, filed Oct. 21, 2019, which is incorporated herein by reference in its entirety. This application claims priority under 35 USC 119 to German Patent Application No. 10 2018 008 356.0, filed Oct. 22, 2018.

BACKGROUND OF THE DISCLOSURE

Technical Field of Disclosure

The present disclosure relates to a system, computer system, and computer program for determining one or more cardiovascular parameters of a patient, which is configured to interact with an apparatus for extracorporeal blood treatment.

Description of Related Art

Extracorporeal blood treatment is indicated for a number of disorders in patients, for example hemodialysis for kidney and liver diseases and extracorporeal membrane oxygenation (ECMO) in the treatment of severe lung diseases (acute respiratory distress syndrome, ARDS) and heart diseases (myocardial infarction, severe arrhythmias). Extracorporeal membrane oxygenation is part of the standard therapy for stabilizing the circulation and/or respiratory function of patients with ARDS and life-threatening hypoxemia. In ECMO, large-volume veins are cannulated using the Seldinger technique, so that blood can flow between the patient and the ECMO machine. In the ECMO apparatus, the blood is perfused by means of a pump using a membrane oxygenator. The latter houses a semipermeable membrane via which the gas exchange takes place in that the blood of the patient flows on one side and oxygen is introduced on the other side. The pump produces a blood flow of 2 to 6 L/min, so that efficient oxygenation and carbon dioxide elimination is possible.

Most often, access to the vascular system of the patient is via the femoral blood vessels. Depending on the underlying disease of the patient, veno-venous, arterio-venous, and veno-arterial cannulation are possible for establishing the ECMO. Arterio-venous cannulation is used in patients who only have disturbed gas exchange, i.e. they have stable circulation and good cardiac function (avECMO; with intact cardiac function, operation without a pump may be possible). The blood flow from the femoral artery is returned to the right atrium via the oxygenator. On the other hand, there is veno-arterial ECMO (vaECMO), which permits complete cardiac support. Venous drainage takes place via the inferior vena cava; from there the blood enters the oxygenator and then travels back to the patient via the femoral artery or the ascending aorta. Using the drainage of the right atrium, vaECMO can achieve biventricular relief and, in addition, can treat co-occurring lung failure. Veno-venous cannulation is most commonly used; vvECMO provides lung support for gas exchange in the lungs. The blood of the patient flows through a cannula located in the inferior vena cava to the oxygenator and from there via the superior vena cava back into the circulatory system of the patient.

Although the method has been used for many decades, prospective randomized studies in ARDS patients in whom the use of ECMO was compared to conventional treatment have so far indicated that ECMO provides only marginal improvement in outcome with a controversial survival benefit. Strategies for improving the effectiveness of ECMO include optimized patient selection, less invasive techniques, and combining ECMO with ultra-protective ventilation. It is also postulated that optimizing the hemodynamic situation of the patient prior to the actual ECMO can help to better integrate patients into ECMO and to optimally adapt ECMO configuration. The extracorporeal blood flow in ECMO, which is adjusted to cardiovascular parameters of the patient such as, e.g., the cardiac output (CO), is of great importance for effective oxygen supply to the blood. Optimizing the hemodynamic situation of the patient requires precise measurement of cardiovascular parameters prior to and during ECMO, for example by means of indicator dilution techniques such as thermodilution. Pulmonary-arterial and transpulmonary thermodilution measurements during ECMO treatment can lead to an incorrect assessment of cardiovascular parameters, however, since extracorporeal circulation can cause an indicator loss in the vascular system of the patient. For example, the cardiac output calculated from such measurements can be greater than the actual cardiac output. It is therefore an object of the present disclosure to record, minimize, and correct as much as possible the error in the determination of cardiovascular parameters, such as, e.g., CO, during treatment with an extracorporeal blood treatment apparatus, e.g., during ECMO treatment. The disclosed system increases the accuracy and reliability of the determination of cardiovascular parameters such as, e.g., CO, during treatment with an extracorporeal blood treatment apparatus; thus, patients are better integrated into the corresponding extracorporeal blood treatment apparatus and the configuration thereof can be optimally adjusted.

SUMMARY OF THE DISCLOSURE

In a first aspect, the disclosure relates to a system for determining a cardiovascular parameter of a patient. The system can also advantageously be configured to determine several cardiovascular parameters of a patient. The system is configured to interact with an apparatus for extracorporeal blood treatment which is connected to the venous vascular system of the patient via an inflow line and an outflow line. The extracorporeal blood treatment apparatus can be, for example, a device for hemodialysis, a device for liver support, or an extracorporeal apparatus for decarboxylation or membrane oxygenation. The inflow line supplies blood from the vascular system of the patient to the blood treatment apparatus. For example, in the vvECMO, a "drainage" catheter located in the inferior vena cava conducts venous blood to the membrane oxygenator. The treated blood is returned to the vascular system of the patient via the outflow line; for example, in vvECMO, a catheter located in the jugular vein or in the superior vena cava conducts oxygen-rich blood to the right atrium. The extracorporeal blood treatment apparatus has at least one pump arranged between the inflow line and the outflow line for moving the blood of the patient within the extracorporeal blood treatment apparatus, wherein the pump conveys the blood via the corresponding treatment unit, e.g., the dialysis membrane or the decarboxylator/oxygenator. The system has temperature influencing means for causing an initial, local temperature deviation $T_1$ in the vicinity of a first point in the vascular system of the patient. Using the temperature influencing means, a traveling temperature change is introduced into the blood flow of the patient. For example, the temperature influencing means can change the temperature in a central vein of the vascular system of the patient, such as, e.g., in the jugular vein or in the femoral vein. The system further includes a first temperature sensor for measuring the local temperature of the blood of the patient at a second point of the vascular system of the patient downstream of the first point, and a second temperature sensor for measuring the local temperature of the blood of the patient in the inflow line of the extracorporeal blood treatment apparatus. The first temperature sensor preferably detects the temperature of the blood of the patient in the arterial vascular system located downstream of the venous vascular system (transpulmonary thermodilution). The sensors provided can advantageously be configured like known sensors used in dilution measurement methods. A platinum resistance sensor is particularly suitable for measuring the temperature, but other thermoresistors or thermocouples are also suitable. A computer system connected to the first and the second temperature sensors is configured to record the local blood temperature, which is measured at the second point of the vascular system of the patient and in the inflow line of the extracorporeal blood treatment apparatus, in each case as a function of time, and to determine and evaluate accordingly a first and a second thermodilution curve ($TDK_1$, $TDK_2$). The technical program device for carrying out steps for evaluating thermodilution is known per se from the prior art (e.g., from German patent application DE 4 214 402 A1). The computer system is further configured to use the second thermodilution curve to determine a temperature deviation $T_{EKBV}$, which is to be allocated to the extracorporeal blood treatment apparatus, and to correlate $T_1$ and $T_{EKBV}$ to determine the cardiovascular parameter. After the cardiovascular parameter, for example cardiac output, has been determined, the flow rate of the extracorporeal blood treatment apparatus can be increased or decreased accordingly in order to adjust the pump output to the cardiovascular situation of the patient. For example, the flow rate of the extracorporeal blood treatment apparatus can also only be greatly reduced or set to zero for a short time in order to be able to carry out a measurement without loss of indicators in the extracorporeal circuit.

The system of the present disclosure advantageously permits an indicator loss possibly caused by the extracorporeal circuit to be detected and subsequently corrected so that errors in the determination of cardiovascular parameters such as, e.g., CO, during extracorporeal blood treatment, e.g., during ECMO treatment, are minimized and thus the accuracy and reliability of the determination is increased. The system of the present disclosure can be used independently of the arrangement/flow direction of the specific extracorporeal blood treatment apparatus and thus is quite versatile. The patient is better integrated into the extracorporeal blood treatment apparatus and the configuration of the latter is optimally adjusted to the cardiovascular condition of the patient.

In a further aspect of the system according to the present disclosure, the first point of the vascular system of the patient, in the vicinity of which first point the temperature influencing means cause the initial, local temperature deviation $T_1$, can be located upstream of the inflow line of the extracorporeal blood treatment apparatus. The term "upstream" refers to the direction of flow in the inflow line of the blood treatment apparatus. For example, the inflow line of the blood treatment apparatus can be disposed in the inferior vena cava, preferably below the convergence of the hepatic vein, while the temperature deviation is caused in the jugular vein. The arrangement leads to the least possible interference by the system of the present disclosure in the extracorporeal blood treatment apparatus, so that, e.g., the number of measurement cycles required is advantageously kept low.

In a preferred further aspect of the system of the present disclosure, the extracorporeal blood treatment apparatus can be a blood treatment apparatus with a pump that provides a flow rate of>100 mL/min, the pump can particularly preferably provide a flow rate of>200 mL/min, and the pump can most particularly preferably provide a flow rate of>300 mL/min. The extracorporeal blood treatment apparatus can preferably be a device for decarboxylation or for membrane oxygenation (ECMO). Particularly in the case of extracorporeal blood treatment apparatus with a high flow rate, the system of the present disclosure can be used to increase the accuracy of the determination of cardiovascular parameters, since the possible loss of the indicator (e.g., the traveling temperature change or the dye) into the corresponding apparatus caused by these apparatus is recorded accurately and effectively and can subsequently be corrected.

In a further aspect of the system of the present disclosure, the computer system can be configured to determine, from the relationship between $T_{EKBV}$ and $T_1$, the proportion $A_{reEKBV}$ of the traveling temperature change recirculating through the extracorporeal blood treatment apparatus. For example, when the flow rate of the blood treatment apparatus is elevated, an indicator (e.g., a traveling temperature change or a dye indicator) can largely branch off from the first point of the vascular system of the patient directly into the inflow line ("drainage catheter") of the apparatus. By comparing the temperature deviation $T_{EKBV}$ to be allocated to the extracorporeal blood treatment apparatus with $T_1$, the proportion $A_{reEKBV}$ of the traveling temperature change recirculating in the blood treatment apparatus can be determined as a percentage. The value $A_{reEKBV}$ can advantageously be used to correct the cardiovascular parameter to be determined; alternatively, the value can be used to adjust system parameters, for example the flow rate of the extracorporeal blood treatment apparatus, for a re-measurement or for continuous operation.

In a preferred aspect of the system of the present disclosure, the temperature influencing means can be manual or automated injection means for injecting a liquid, a temperature of the liquid differing from the temperature of the blood of the patient. The temperature influencing means can in particular be suitable for injecting an appropriately temperature-controlled liquid bolus. Preferably, the temperature, time, and, particularly preferably, also duration of the bolus injection are measured by a further, third temperature sensor which is arranged, for example, within or in the immediate vicinity of the temperature influencing means, and are supplied to the computer system via corresponding connecting means.

In a preferred further aspect of the system of the present disclosure, the first thermodilution curve can be determined by means of transpulmonary thermodilution. In the transpulmonary thermodilution measurement known from the prior art, to determine the thermodilution curve a thermal indicator bolus is injected into the upper vena cava (V. cava sup.) of a patient and the temperature response is measured at a point in the circulation of the body of the patient, e.g., in the femoral artery of a patient. A large number of vascular parameters can advantageously be determined from the thermodilution curve obtained, for example the cardiac output CO, global end-diastolic volume (GEDV), intrathoracic blood volume (ITBV), etc., and a number of other parameters and indices can be derived therefrom, e.g., extravascular lung water EVLW, a parameter for impending pulmonary edema, is also calculated. In addition, the contractility of the heart muscle can be assessed ($dP_{max}$, GEF, CPI). In particular, the one cardiovascular parameter can be cardiac output (CO), extravascular lung water (EVLW), or global end-diastolic volume (GEDV). These can be calculated in a known manner from the arterial thermodilution curve TDK; in particular, the cardiac output $CO_{TDart}$, appearance time AT, mean transit time $MTD_{TDart}$, and exponential fall time $DST_{TDart}$ can be calculated.

In a further aspect of the system of the present disclosure, the computer system can be configured to correlate $T_1$ and $T_{EKBV}$ and the area under the first thermodilution curve ($TDK_1$) for calculating cardiac output.

In particular, in an aspect of the system of the present disclosure, the flow rate of the blood treatment apparatus is known, while the cardiac output and the temperature change not branched off into the blood treatment apparatus are unknown. The cardiac output can be calculated using the relationship of the flow rate to the quotient of the temperature deviation in the vascular system of the patient ($T_1$-$T_{EKBv}$) and the area under the first thermodilution curve. The GEDV and other cardiovascular parameters, for example, can be calculated from this variable and from the variables derived from $TDK_1$ (MTT, DST).

In a preferred aspect of the system of the present disclosure, the computer system can also be configured to interact with the pump of the extracorporeal blood treatment apparatus such that $A_{reEKBv}$<30% when determining the one or more cardiovascular parameters. This can be achieved, for example, in that the computer system controls the pump and the pump output is reduced accordingly or temporarily suspended. When determining the one or more cardiovascular parameters, it is preferred that $A_{reEKBV}$<20%, particularly preferably $A_{reEKBV}$<10%.

In a specific further aspect of the system of the present disclosure, the first point of the vascular system of a patient, in the vicinity of which point the temperature influencing means cause an initial local temperature deviation, and the inflow line of the extracorporeal blood treatment apparatus are located cranially with respect to a plane in which the heart valves of the patient are located. The arrangement is advantageous because for the specific measuring arrangement, with regard to the calculation of a number of cardiovascular parameters, there are already constants to be considered empirically. For example, the constants $K_1$ and $K_2$ to be inserted into the Steward-Hamilton equation $$CO = \frac{V_L(T_B - T_L)K_1 K_2}{\int \Delta T_B(t)dt}$$

are known for the correspondingly carried out transpulmonary thermodilution, i.e., for an arrangement in which the temperature bolus is injected via the jugular vein into the superior vena cava and detected in the femoral artery of a patient.

In a second aspect, the present disclosure relates to a computer system which is configured to cooperate with a connected apparatus for extracorporeal blood treatment, which apparatus is connected to the venous vascular system of the patient via an inflow line and an outflow line, the computer system having the following: first connecting means to connect the computer system to temperature influencing means; second connecting means to connect the computer system to a first temperature sensor; third connecting means to connect the computer system to a second temperature sensor. The computer system further comprises access means for accessing executable commands in order to cause the computer system to control temperature influencing means in order to cause an initial local temperature deviation $T_1$ in the vicinity of a first point of the vascular system of a patient, thereby introducing a traveling temperature change in the blood flow of the patient. The first point is preferably located upstream of an inflow line of an extracorporeal blood treatment apparatus. The computer system furthermore records the local temperature of the blood of the patient, which temperature is measured at a second point in the vascular system of a patient downstream of the first point by means of a first temperature sensor, as a function of time, in order to determine a first thermodilution curve ($TDK_1$), as well as the local temperature of the blood of the patient, which temperature is measured in the inflow line of the extracorporeal blood treatment apparatus, recorded as a function of time, in order to determine a second thermodilution curve ($TDK_2$). Furthermore, from the second thermodilution curve, the computer system determines a temperature deviation $T_{EKBV}$ which is to be allocated to the extracorporeal blood treatment apparatus and correlates $T_1$ and $T_{EKBV}$ to determine one or more cardiovascular parameters.

In a third aspect, the disclosure relates to a non-transitory computer-readable storage medium. The disclosed non-transitory computer-readable storage medium includes computer-readable instructions embodied therein that are executable by a computer to cause the computer to carry out a variety of method steps, including any of the methods described herein. In particular, the disclosed non-transitory computer-readable storage medium comprises computer-readable instructions for determining a cardiovascular parameter of a patient by means of thermodilution measurements in a system which is configured to interact with an apparatus for extracorporeal blood treatment, which apparatus is connected to the venous vascular system of the patient. The computer-readable instructions are executable by a computer system in order to cause the computer system to control temperature influencing means which are connected to the computer system in order to cause an initial local temperature deviation $T_1$ in the vicinity of a first point of the vascular system of a patient. The first point is preferably located upstream of the inflow line of the extracorporeal blood treatment apparatus which is connected to the venous system of the patient via an inflow line and an outflow line. The initial local temperature deviation $T_1$ introduces a traveling temperature change in the blood flow of the patient. The computer system records the local temperature of the blood of the patient, which temperature is measured at a second point in the vascular system of the patient, downstream of the first point, by means of a first temperature sensor, as a function of time, in order to determine a first thermodilution curve $TDK_1$. Furthermore, the local temperature of the blood of the patient, which temperature is measured in the inflow line of the extracorporeal blood treatment apparatus by means of a second temperature sensor, is recorded as a function of time, in order to create a second thermodilution curve $TDK_2$. The second thermodilution curve finally determines a temperature deviation $T_{EKBV}$ which is to be allocated to the extracorporeal blood treatment apparatus, and $T_1$ and $T_{EKBV}$ are correlated to determine the one cardiovascular parameter.

Examples of preferred embodiments of the present disclosure are explained in more detail below with reference to the accompanying drawing.

The drawing is purely schematic and, for reasons of clarity, is not true to scale. In particular, the relations between the dimensions, especially diameters, tube lengths, and external dimensions may differ from actual embodiments. In practice, the dimensions can be dimensioned based on the requirements in individual cases and based on common standard parts.

BRIEF DESCRIPTION OF THE FIGURE

FIG. 1 shows a schematic overview of the measuring arrangement of the present disclosure in a preferred embodiment and the vascular system of a patient.

DESCRIPTION OF NON-LIMITING EMBODIMENTS OF THE DISCLOSURE

FIG. 1 shows a schematic overview of an aspect of the disclosed measuring arrangement and the vascular system of a patient, wherein the apparatus for extracorporeal blood treatment (10) is connected to the venous vascular system of the patient via an inflow line (11; "drainage") and an outflow line (12). The extracorporeal blood treatment apparatus can be, for example, an apparatus for extracorporeal membrane oxygenation (vvECMO, as shown in FIG. 1) or an apparatus for liver dialysis. The inflow line (11) is introduced, for example, via the femoral vein and comes to rest in the inferior vena cava (V. cava inferior) below the convergence of the hepatic vein. The outflow line (12) is introduced, for example, via the jugular vein and comes to rest in the superior vena cava (V. cava superior) immediately in front of the right atrium. In the case of ECMO, low-oxygen, venous blood is supplied to the blood treatment apparatus via the inflow line (11), while the oxygenated blood reaches the right atrium via the outflow line (12). The inventive system can also be used in situations in which a vaECMO is used, in which the deoxygenated blood is conducted via the femoral vein to the ECMO and the oxygenated blood is returned to the vascular system of the patient via the femoral artery. In this arrangement, the ECMO takes over the entire pumping output.

The cardiovascular parameter is determined by means of thermodilution; several cardiovascular parameters can also be determined and/or calculated by means of thermodilution. The disclosed temperature influencing means (20) are preferably an injection device by means of which a cooled liquid is injected as a bolus into the vascular system of the patient. In principle, the temperature change can be generated at any point in the central venous vascular system of the patient. The outflow line of the ECMO (via which oxygenated blood is supplied to the vascular system of the patient) and the first point (31) are preferably cranial with respect to the plane of the heart valve. As shown in FIG. 1, it is particularly preferred to perform a bolus injection for the thermodilution measurement at a first point (31), e.g., the jugular vein, upstream of the inflow line (11) of the ECMO. A traveling temperature change generated in the jugular vein travels via the right heart and pulmonary circulation into the left heart and from there via the aorta into the systemic circulation. The initial temperature deviation $T_1$ generated by the bolus injection is calculated or measured, e.g., using a corresponding algorithm. The temperature influencing means can preferably detect the temperature, time, and possibly also duration of the bolus injection, for example by means of a temperature sensor which is arranged within or in the immediate vicinity of the temperature influencing means. The temperature influencing means can preferably supply the measurement results to a computer system (40) which is connected to the disclosed system via connecting means. The first temperature sensor (21) for measuring the local temperature of the blood of the patient is arranged at a second point (32) of the vascular system of the patient, downstream of the first point (31), in this case e.g., in the femoral artery. A further temperature sensor (22) is arranged in the inflow line (11) of the extracorporeal blood treatment apparatus. Depending on the flow rate of the extracorporeal blood treatment apparatus, e.g., at a high flow rate>500 mL/min, or depending on the pointal relationship between the injection site/inflow to the line, a part of the injected temperature bolus branches off into the extracorporeal circuit. This part of the injected temperature bolus is recorded by the second temperature sensor (22). The computer system (40) connected to the first (21) and second temperature sensor (22) via connecting means records the detected temperature as a function of time and correspondingly determines a first and a second thermodilution curve ($TDK_1$, $TDK_2$). The technical program device for carrying out evaluation steps of a thermodilution is known per se from the prior art (e.g., from German laid-open specification DE 4 214 402 A1). The computer system is furthermore configured to determine from the second thermodilution curve $TDK_2$ a temperature deviation $T_{EKBV}$ which is to be allocated to the extracorporeal blood treatment apparatus, and $T_1$ and $T_{EKBV}$ for determining the cardiovascular parameter. The system of the present disclosure advantageously enables an indicator loss, possibly caused by the extracorporeal circuit, to be detected and subsequently corrected so that errors in the determination of cardiovascular parameters, such as, e.g., the CO, during an extracorporeal blood treatment, e.g., during ECMO treatment, can be minimized and thus the accuracy and reliability of the determination is increased. The system of the present disclosure can be used independently of the arrangement/flow direction of the specific extracorporeal blood treatment apparatus and is therefore versatile. The patient is better integrated into the extracorporeal blood treatment apparatus and the configuration of the latter is optimally adjusted to the cardiovascular condition of the patient.

In a further embodiment of the system of the present disclosure, the first point of the vascular system of the patient, in the vicinity of which point the temperature influencing means cause the initial local temperature deviation $T_1$, can be located in the vicinity of a first point of the vascular system of the patient upstream of the inflow line (11) of the extracorporeal blood treatment apparatus. The term "upstream" refers to the direction of flow in the inflow line of the blood treatment apparatus. For example, the inflow line of the blood treatment apparatus can be located in the inferior vena cava, while the temperature deviation is caused in the jugular vein. The arrangement leads to the least possible interference by the system of the present disclosure in the extracorporeal blood treatment apparatus, so that, e.g., the number of measurement cycles required is advantageously kept low.

The invention claimed is:

1. A system for determining a cardiovascular parameter of a patient, configured to interact with an apparatus for extracorporeal blood treatment connected to a venous vascular system of a vascular system of the patient via an inflow line attached at a first point in the venous vascular system and an outflow line attached at a second point in the venous vascular system, wherein the extracorporeal blood treatment apparatus comprises at least one pump arranged between the inflow line and the outflow line for moving the blood of the patient within the extracorporeal blood treatment apparatus, the system comprising:

a. a temperature influencing means for causing an initial local temperature deviation ($T_1$) in the vicinity of the second point of the venous vascular system of the patient, so that a traveling temperature change is introduced in the blood flow of the patient;

b. a first temperature sensor for measuring an intracorporeal temperature of the blood of the patient at a third point in the vascular system of the patient downstream of the second point;

c. a second temperature sensor for measuring a local temperature of the blood of the patient in the inflow line of the extracorporeal blood treatment apparatus; and d. a computer system connected to the first temperature sensor and the second temperature sensor and configured to record the local temperature of the blood of the patient at the third point in the vascular system of the patient and the local temperature of the blood of the patient in the inflow line of the extracorporeal blood treatment apparatus as a function of time, and to determine and evaluate a first and a second thermodilution curve ($TDK_1$, $TDK_2$), and wherein the computer system is further configured to determine, from the second thermodilution curve, a temperature deviation ($T_{EKBV}$) which is to be allocated to the extracorporeal blood treatment apparatus, and to correlate $T_1$ and $T_{EKBV}$ to determine the cardiovascular parameter.

2. The apparatus according to claim 1, wherein the second point in the venous vascular system of the patient is located upstream of the first point in the venous vascular system of the patient.

3. The apparatus according to one of claim 1, wherein the extracorporeal blood treatment apparatus is a blood treatment apparatus with a pump providing a flow rate of >100 mL/min.

4. The apparatus according to claim 3, wherein the computer system is configured to determine, from the relation of $T_{EKBV}$ and $T_1$, a proportion ($A_{reEKBV}$) of a traveling temperature change recirculating through the extracorporeal blood treatment apparatus.

5. The apparatus according to claim 1, wherein the temperature influencing means comprise an injection means for injecting a liquid, a temperature of the liquid differing from the temperature of the blood of the patient.

6. The apparatus according to claim 1, wherein the first thermodilution curve is determined by means of transpulmonary thermodilution.

7. The apparatus according to claim 1, wherein the cardiovascular parameter is cardiac output (CO), extra vascular lung water (EVLW), or global end-diastolic volume (GEDV).

8. The apparatus according to claim 6, wherein the computer system is configured to correlate $T_1$ and $T_{EKBV}$ and the area under the first thermodilution curve for calculating cardiac output.

9. The apparatus according to claim 4, wherein the computer system is also configured to interact with the pump of the extracorporeal blood treatment apparatus such that when determining the cardiovascular parameter the $A_{reEKBV}$ is less than 30%.

10. The apparatus according to claim 1, wherein the second point in the venous vascular system of a patient, in the vicinity of which point the temperature influencing means cause an initial local temperature deviation, and the outflow line of the extracorporeal blood treatment apparatus are located cranially with respect to a plane in which the heart valves of the patient are located.

11. A computer system configured to interact with an apparatus for extracorporeal blood treatment, the apparatus connected to a venous vascular system of a vascular system of a patient via an inflow line attached at a first point in the venous vascular system and an outflow line attached at a second point in the venous vascular system, the computer system comprising:

a first connecting means for connecting the computer system to a temperature influencing means;

a second connecting means for connecting the computer system to a first temperature sensor;

a third connecting means for connecting the computer system to a second temperature sensor; and an access means for accessing executable commands in order to cause the computer system:

a. to control the temperature influencing means to cause an initial local temperature deviation ($T_1$) in the vicinity of the second point in the venous vascular system of the patient, thereby introducing a traveling temperature change in the blood flow of the patient;

b. to record an intracorporeal temperature of the blood of the patient measured at a third point in the vascular system of the patient downstream of the second point by means of the first temperature sensor, as a function of time, in order to determine a first thermodilution curve ($TDK_1$);

c. to record a local temperature of the blood of the patient measured in the inflow line of the extracorporeal blood treatment apparatus as a function of time, in order to determine a second thermodilution curve ($TDK_2$); and d. to determine from the second thermodilution curve a temperature deviation $T_{EKBV}$ which is to be allocated to the extracorporeal blood treatment apparatus, and to correlate $T_1$ and a temperature deviation ($T_{EKBV}$) to determine a cardiovascular parameter.

12. A non-transitory computer-readable storage medium with computer-readable instructions stored thereon for determining a cardiovascular parameter of a patient by means of thermodilution measurements in a system configured to interact with an apparatus for extracorporeal blood treatment, the apparatus connected to a venous vascular system of a vascular system of the patient, the computer-readable instructions being executable by a computer system to cause the computer system:

a. to control a temperature influencing means connected to the computer system to cause an initial local temperature deviation $T_1$ in the vicinity of a first point in the venous vascular system of the patient, so that a traveling temperature change is introduced in the blood flow of the patient;

b. to measure an intracorporeal temperature of the blood of the patient measured at a second point in the vascular system of the patient downstream of the first point by means of a first temperature sensor, recorded as a function of time, in order to determine a first thermodilution curve ($TDK_1$);

c. to record a local temperature of the blood of the patient measured in an inflow line of the extracorporeal blood treatment apparatus attached at a third point in the vascular system by means of a second temperature sensor, as a function of time, in order to determine a second thermodilution curve ($TDK_2$); and d. to determine from the second thermodilution curve a temperature deviation ($T_{EKBV}$) which is to be allocated to the extracorporeal blood treatment apparatus, and to correlate $T_1$ and $T_{EKBV}$ to determine the cardiovascular parameter.

* * * * *